(12) United States Patent
Mach et al.

(10) Patent No.: US 6,676,925 B1
(45) Date of Patent: *Jan. 13, 2004

(54) SIGMA-2 RECEPTORS AS BIOMARKERS OF TUMOR CELL PROLIFERATION

(75) Inventors: Robert H. Mach, Winston-Salem, NC (US); Kenneth T. Wheeler, Winston-Salem, NC (US); Biao Yang, Winston-Salem, NC (US); Steven R. Childers, Winston-Salem, NC (US)

(73) Assignee: Wake Forest University, Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/528,398

(22) Filed: Mar. 20, 2000

Related U.S. Application Data (63) Continuation of application No. 09/142,935, filed as application No. PCT/US97/04403 on Mar. 19, 1997, now Pat. No. 6,113,877.
(60) Provisional application No. 60/013,717, filed on Mar. 20, 1996.

(51) Int. Cl.$^7$ .............................................. A61K 49/00
(52) U.S. Cl. ...................... 424/9.1; 424/1.11; 424/1.65; 424/1.81; 424/1.85; 514/212.01; 546/124; 546/184; 546/125; 546/1; 540/1
(58) Field of Search ............................. 424/1.11, 1.65, 424/1.81, 9.1, 9.3, 9.4, 9.6, 9.7, 1.85, 9.8; 534/7, 10–14, 15, 16; 546/1, 26, 124, 112, 125, 129, 152, 184; 514/212.01, 183; 540/1

(56) References Cited

U.S. PATENT DOCUMENTS

| | | | | |
|---|---|---|---|---|
| 4,797,387 A | * | 1/1989 | King | 514/212 |
| 4,808,588 A | | 2/1989 | King | 514/212 |
| 4,983,600 A | * | 1/1991 | Ward et al. | 514/214 |
| 5,106,843 A | | 4/1992 | Ward et al. | 514/213 |
| 5,330,990 A | | 7/1994 | Hansen | 514/299 |
| 5,436,251 A | | 7/1995 | Ward et al. | 514/304 |
| 6,113,877 A | * | 9/2000 | Mach et al. | 424/1.65 |

OTHER PUBLICATIONS

Bermudez, J., et al., "5–Hydroxytryptamine (5–HT3) Receptor Antagonists. 3. Ortho–substituted Phenylureas", *J. Med. Chem., 33,* 1932–1935, (1990).

Bermudez, J., et al., "5–Hydroxytryptamine (5–IIT3) Receptor Antagonists. 3. Ortho–substituted Phenylureas", *J. Med. Chem.,* 33, pp. 1932–1935, (1990).

Holum, J., "Elements of General, Organic and Biological Chemistry", *Ninth Edition, Periodic Law and Periodic Table,* 42–45, (1995).

Kline, R.H., et al., "Synthesis of 3–carbamoylecgonine Methyl Ester Analogues as Inhibitors of Cocaine Binding and Dopamine Uptake", *J. Med. Chem.,* 34, pp. 702–705, (1991).

Turconi, M., et al., "Synthesis of a New Class of 2, 3–Dihydro–2–oxo–1H–benzimidazole–1carboxylic Acid Derivatives as Highly Potent 5–HT3 Receptor Antagonists", *J. Med. Chem.,* 33, pp. 2101–2108, (1990).

* cited by examiner

*Primary Examiner*—Dameron Jones
(74) *Attorney, Agent, or Firm*—Myers Bigel Sibley & Sajovec, PA (57) ABSTRACT

Detectably-labeled compounds of formula (I) wherein A,B,C,D,E,F,R,X,Y and Z have any of the meanings given in the specification, and their pharmaceutically acceptable salts, are useful in competitive assays to assay for the presence of 2 receptors. Also disclosed are pharmaceutical compositions containing such a compound of formula (I), methods for their use and intermediates useful for preparing such compounds of formula (I).

15 Claims, 3 Drawing Sheets

Figure 1

Compound 2

Compound 3

Compound 4

Compound 5

Figure 2

Compound 6

Compound 7

Compound 8

Compound 9

Compound 10

R = methyl or benzyl

SIGMA-2 RECEPTORS AS BIOMARKERS OF TUMOR CELL PROLIFERATION

This application is a Continuation of U.S. Ser. No. 09/142,935, filed Sep. 17, 1998, now U.S. Pat. No. 6,113,877 which is a 371 of PCT Application No. PCT/US97/04403, filed Mar. 19, 1997, which claims priority to U.S. Provisional Application No. 60/013,717, filed Mar. 20, 1996.

BACKGROUND OF THE INVENTION

Breast cancer is characterized by a proliferative potential that can vary considerably from patient to patient. The rate of cell proliferation has been shown in breast tumors to predict the response to radiation therapy and chemotherapy. Presently, measures of cell proliferation are obtained by histological or flow-cytometric analysis. Both methods are limited by sampling procedures and only 60–70% of patient samples are suitable for flow cytometric analysis.

It was recently demonstrated that sigma-2 (σ2) receptors are expressed in high density in a number of human and rodent breast cancer cell lines (*Cancer Research*, 55, 408 (1995)). However, their expression is heterogenous, and their function is unknown.

A continuing need exists for noninvasive methods that can accurately assess the proliferative status of breast cancer. Such methods could have a significant impact on determining an optimal therapy for treating breast cancer patients.

SUMMARY OF THE INVENTION

The present invention provides a noninvasive method to detect cancer cells or to assess the proliferative status of cancer cells which express sigma-2 (σ2) receptors, such as cells of solid tumors, in vitro or in vivo. The method preferably comprises (a) administering to a human patient afflicted with a solid tumor, such as breast cancer, an amount of a detectably labeled compound of formula (I):

(I)

wherein R is $(C_1-C_4)$alkyl, $C_6F_5CH_2$, $C_6H_5$, or T—$C_6H_4CH_2$ wherein T is halo (Br, Cl, I, F),$CH_3S$, $CH_3O$, $NH_2$ or H; A is NH, O, or S; B is NH, O, or S; C is O or S; D is CH or N; E is CH or N; F is CH or N; Y and Z are individually H, halo, OH, $(C_1-C_4)$alkyl, $(C_1-C_4)$alkoxy, $(C_1-C_4)C(O)$, $(C_1-C_4)$alkylS, $NH_2$, SH, $N(R)_2$ or together are $OCH_2O$; X is $(CH_2)_2$, $(CH_2)_3$ or CH=CH; or a pharmaceutically acceptable salt thereof; and (b) determining the extent to which the compound of formula (I) binds to cells of said cancer, said extent providing a measure of the presence and/or proliferative status of said cells, which status correlates to the extent of sigma-2 receptor expression by said cells. The method is based on the ability of the compounds of formula (I) to selectively bind to sigma-2 (σ2) receptors, versus σ1 receptors.

Groups Z and Y can occupy any ring position, i.e., any one of E, D or F can be CY or CZ. Preferably, at least one of Y or Z is not H. Preferably A is O and B is NH. Preferably, R is $CH_3$, benzyl or phenyl. Alkyl can be branched, unbranched, cycloalcyl or (cycloalkyl)alkyl.

Preferably, the label is a fluorescent label or radionuclide, such as a radioisotope of halogen ($^{125}$I, $^{123}$I, $^{18}$F, $^{19}$F) or $^{11}$C. The compound is preferably administered parenterally, i.e., by intravenous, i.p., intrathecal or enteral administration.

Novel compounds of formula (I), labeled and unlabeled, are also within the scope of the invention, as are pharmaceutical compositions comprising one or more of said compounds. The unlabeled compounds can be used as intermediates to make labeled compounds or as sigma-2 specific ligands which can be used in competitive assays to assay for the presence of σ2 receptors, as described below. The configuration at the 3-position can be exo- or endo-; of which endo- is referred.

DETAILED DESCRIPTION OF THE INVENTION

Processes for preparing compounds of formula I are provided as further embodiments of the invention and are illustrated by the following procedures in which the meanings of the generic radicals are as given above unless otherwise qualified.

Compounds of formula I wherein A is oxygen and B is nitrogen can generally be prepared by reacting an isocyanate of formula II with an alcohol of formula III under standard conditions.

Solvents, bases, and reaction conditions suitable for such a reaction are well known to the art. For example, the reaction may conveniently be carried out under conditions similar to those described in Example 1.

Compounds of formula I wherein A is nitrogen and B is nitrogen can generally be prepared by reacting an isocyanate of formula II with an amine of formula IV under standard conditions.

(IV)

Solvents, bases, and reaction conditions suitable for such a reaction are well known to the art.

It is noted that many of the starting materials employed in the synthetic methods described above are commercially available, are reported in the scientific literature, or can be prepared using methods analogous to those described in the literature.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound may be combined with one or more excipients and used in the form of ingestible tablets, buccal tablets, troches, capsules, elixirs, suspensions, syrups, wafers, and the like. Such compositions and preparations should contain at least 0.1% of the compound. The percentage of the compositions and preparations may, of course, be varied and may conveniently be between about 2 to about 60% of the weight of a given unit dosage form. The amount of compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the compound may be incorporated into sustained-release preparations and devices.

The present compounds may also be administered intravenously or intraperitoneally by infusion or injection. Solutions of a compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising a labeled or unlabeled compound of formula I adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the labeled or unlabled compound of formula (I) plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%. Single dosages for injection, infusion or ingestion will generally vary between 50–1500 mg, and may be administered, i.e., 1–3 times daily, to yield levels of about 0.5–50 mg/kg, for adults.

Accordingly, the invention includes a pharmaceutical composition comprising a labeled or unlabeled compound of formula I as described hereinabove; or a pharmaceutically acceptable salt thereof; and a pharmaceutically acceptable diluent or carrier.

Compounds of formula (I) can be labeled using any of a number of techniques which are well known in the art. For example, a radioisotope can be incorporated into said compound or appended to said compound of formula (I) using techniques well known in the art, for example, techniques analogous to those described in Arthur Murry III, D. Lloyd Williams; *Organic Synthesis with Isotopes*, vol. I and II, Interscience Publishers Inc., N.Y. (1958) and Melvin Calvin et al. *Isotopic Carbon* John Wiley and Sons Inc., N.Y. (1949). Preferably, a compound of formula (I) may be labeled by appending a radioisotope of a halogen to the aromatic ring comprising DEF.

Figure 1:
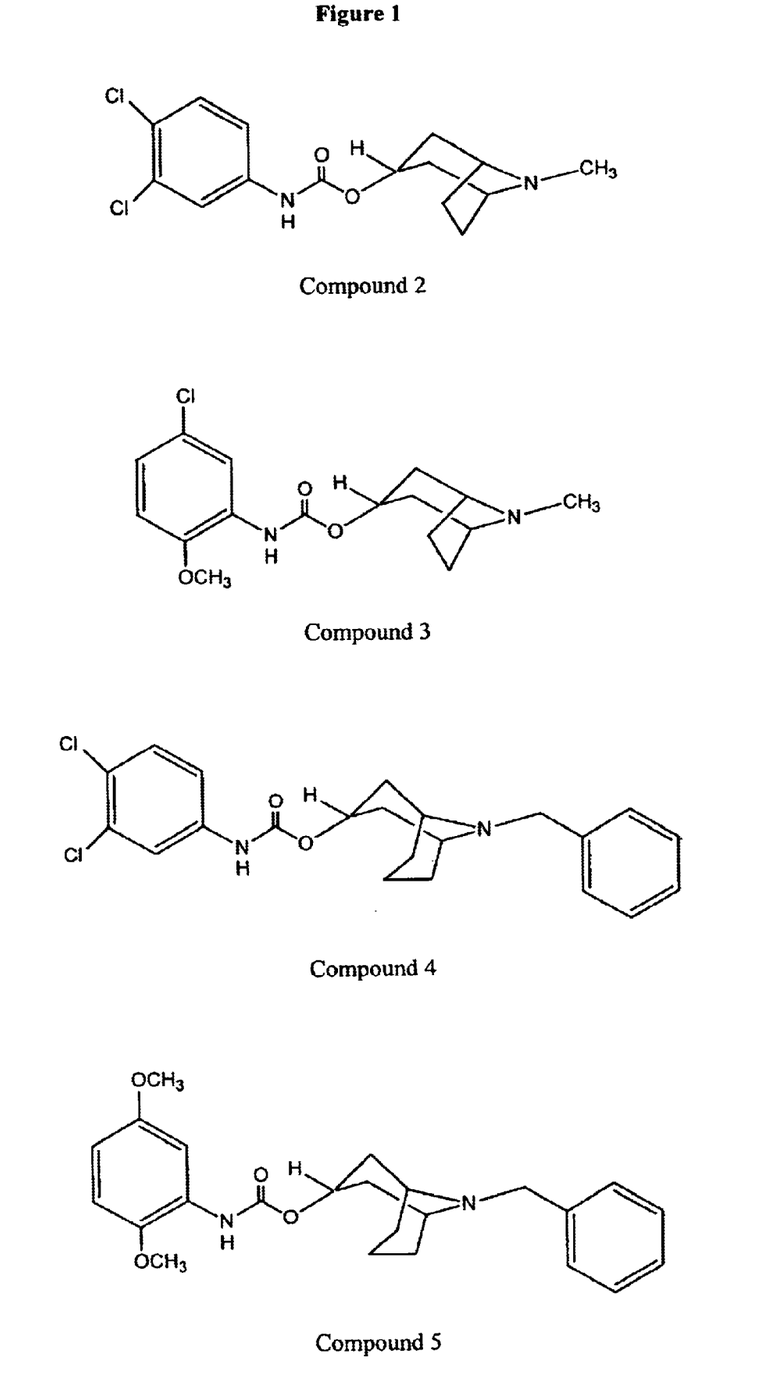
FIG. 1 shows compounds of the invention.
Figure 2:
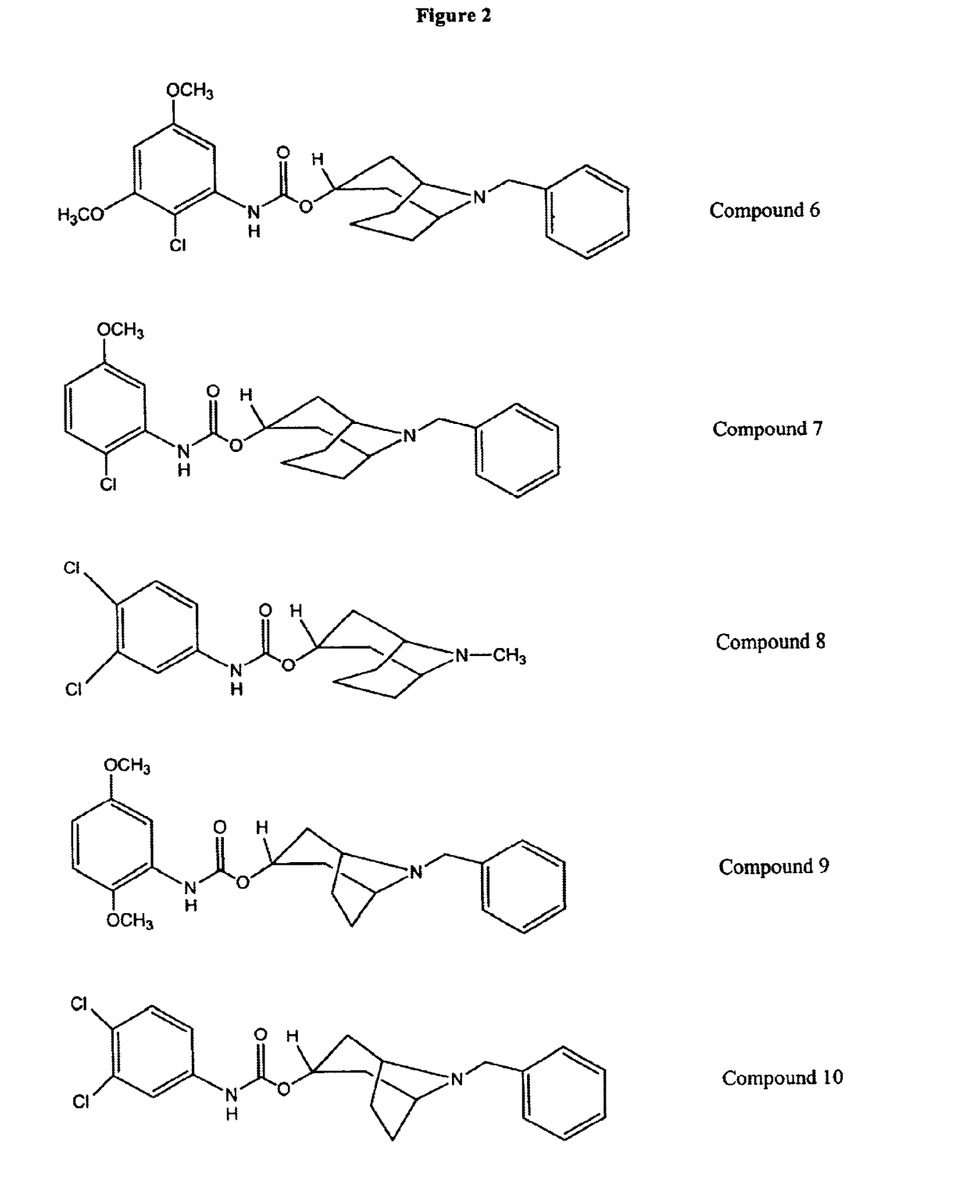
FIG. 2 shows compounds of the invention.
Figure 3:
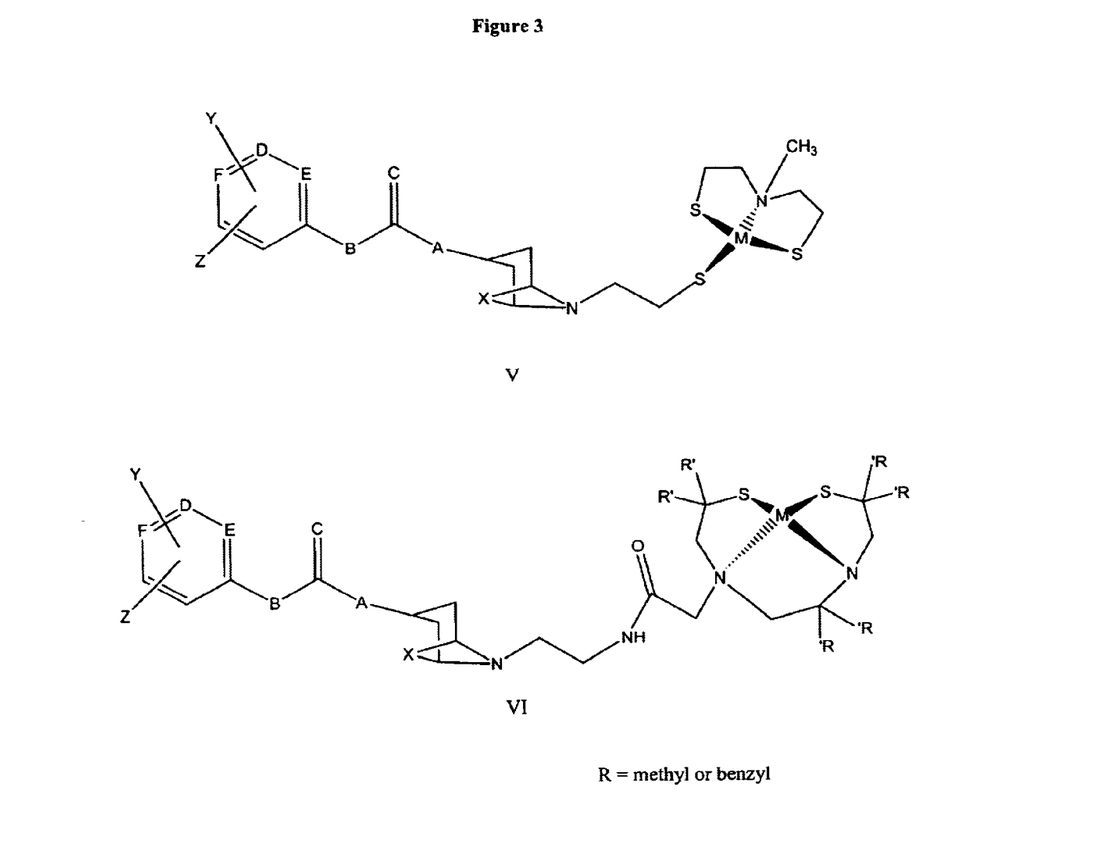
FIG. 3 shows compounds of the invention.

Additionally, a compound of formula (I) can be labeled with a metal chelating group optionally comprising a radionuclide, such as a metallic radioisotope. Such chelating groups are well known in the art and include polycarboxylic acids such as for example diethylenetriaminepentaacetic acid, ethylenediaminetetraacetic acid, and the like, or analogs or homologs thereof, as well as the chelating groups disclosed in S. Meegalla et al. *J. Am. Chem. Soc.* 117 11037–11038, 1995 and in S. Meegalla et al. *Bioconjugate Chem.* 7:421–429, 1996. The chelating group or the radionuclide therein may be attached directly to a compound of formula (I), or may be attached to a compound of formula (I) by means of a divalent or bifunctional organic linker group. Such bifunctional linker groups are well known in the art and are preferably less than 50 angstroms in length. Examples of suitable linker groups include 2-aminoethyl, 2-mercaptoethyl, 2-aminopropyl, 2-mercaptopropyl, ε-amino caproic acid, 1,4-diaminobutane, and the like. Preferably, the bifunctional linker group is attached to a compound of formula (I) at the bridgehead nitrogen which is substituted by the group R in formula (I). A compound of formula (I) bearing a linker group may conveniently be prepared from a compound of formula (I) wherein R is hydrogen by alkylation of the bridgehead nitrogen. Suitable conditions for the alkylation of secondary amines are well known in the art. The linker group may also be attached at any synthetically feasible position. For example, FIG. 3 shows two compounds of the invention (compounds V and VI) which are compounds of formula (I), labeled with a metal chelating group comprising a radionuclide (M).

Any metallic radioisotope capable of being detected in a diagnostic procedure can be employed as a radionuclide. For example, suitable radioisotopes include: Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, 152, Gadolinium-153, Gold-195, Gold-199, Hainium-175, Hafnium-175–181, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-226, Rhemum-186, Rubidium-86, Ruthenium-103, Ruthenium-106, Scandium-44, Scandium46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Titanium-44, Tungsten-185, Vanadium-48, Vanadium-49, Ytterbium-169, Yttrium-88, Yttrium-90, Yttrium-91, Zinc-65, and Zirconium. Preferably, technetium-99m may be useful for SPECT imaging studies, and rhenium-188, rhenium-186, copper-64 and yitrium-90 may be useful for radiotherapy of breast tumors.

The invention will be further described by reference to the following detailed examples.

EXAMPLE 1

In this study, the expression of $\sigma_2$ receptors on proliferative (P) and quiescent (Q) cells of the mouse mammary adenocarcinoma line, 66, was examined. Scatchard analyses of $\sigma_2$ receptors were performed on membrane preparations from 66 P (3 day cultures) and 66 Q (7, 10, 12 day cultures) cells. Cell membranes (30 μg protein) were incubated with 4 nM [$^3$H]1,3-di-o-tolylguanidine ([$^3$H]DTG) and varying amounts of unlabeled DTG (0.1–1000 nM) in the presence of 100 nM (+)-pentazocine, which masks $\sigma_1$, receptors. The Scatchard studies revealed that P cells had about three times more σ2 receptors/cell than the 7 day Q cells and about 10 times more $\sigma_2$ receptors/cell than the 10 day Q cells. Therefore, although >97% of the cells were quiescent after 7 days in culture (*Cell Tissue Kinet*, 17, 65, (1984)), the maximum differential in the $\sigma_2$ expression between 66 P and Q cells was not attained until these cells had been in culture for 10 days (see Table 1).

TABLE 1

|  | P cells | Q cells | P:Q ratio |
|---|---|---|---|
| 7 Day Cells | | | |
| receptors/cell | 5.10 × 10$^5$ | 1.8 × 10$^5$ | 2.8 |
| Kd ± S.E.M. | 56.3 ± 7.3 | 41.6 ± 4.3 | — |
| 10 Day Cells | | | |
| receptors/cell | 8.40 × 10$^5$ | 8.80 × 10$^4$ | 9.8 |
| Kd ± S.E.M. | 43.8 ± 8.1 | 34.0 ± 7.2 | — |

The difference in receptors/cell between the 7 day and 10 day Q cells indicate that prolonged quiescence results in a down regulation of σ2 receptors.

EXAMPLE 2

(3-endo)-8-Methyl-8-azabicyclo[3.2.1]octyl-3-N-(3', 4'-dichlorophenyl)-carbamate (2)

A mixture of tropine hydrate (100 mg, 0.71 mmol) and the 3,4-dichlorophenyl isocyanate (127 mg, 0.71 mmol) in dry toluene (10 mL) was heated under reflux for 2 hours. After cooling, the organic solution was made alkaline with saturated sodium bicarbonate solution and then extracted with chloroform (3×20 mL). The organic layers were combined and dried with sodium sulfate. The solvent was removed under vacuum and the residue crystallized from pentane/ethylacetate to give the title compound.

NMR (CDCl$_3$) d 1.79–2.33 (m, 8H), 2.31 (s, 3H), 3.15 (br s, 2H), 4.98–5.02 (t, 1H), 5.56 (s, 1H), 7.08–7.64 (m, 3H).

EXAMPLE 3

(3-endo)-8-Methyl-8-azabicyclo[3.2.1]octyl-3-N-(2'-methoxy-5'-chloro-phenyl)-carbamate (3)

A mixture of tropine hydrate (100 mg, 0.71 mmol) and the 2-methoxy-5-chlorophenyl isocyanate (118 mg, 0.71 mmol)

in dry toluene (10 mL) was heated under reflux for 2 hours. After cooling, the organic solution was made alkaline with saturated sodium bicarbonate solution and then extracted with chloroform (3×20 mL). The organic layers were combined and dried with sodium sulfate. The solvent was removed under vacuum and the residue crystallized from pentane/ethylacetate to give the title compound.

NMR (CDCl$_3$)δ1.60–2.48 (m, 8H), 3.18 (br s, 2H), 3.94 (s, 3H), 4.99–5.02 (t, 1H), 6.75–8.14 (m, 4H).

EXAMPLE 4

(3-endo)-9-Benzyl-9-azabicyclo[3.3.1]nonanyl-3-N-(3', 4'-dichlorophenyl)-carbamate (4)

A mixture of (3-endo)-9-benzyl-9-azabicyclo[3.3.1] nonanol (100 mg, 0.43 mmol) and the 3,4-dichlorophenyl isocyanate (78 mg, 0.43 mmol) in dry toluene (10 mL) was heated under reflux for 2 hours. After cooling, the organic solution was made alkaline with saturated sodium bicarbonate solution and then extracted with chloroform (3×20 mL). The organic layers were combined and dried with sodium sulfate. The solvent was removed under vacuum and the residue crystallized from pentane/ethylacetate to give the title compound.

NMR (CDCl$_3$)δ1.14–1.58 (m, 4H), 1.92–2.15 (m, 4H), 2.42–2.52 (m, 2H), 3.01–3.07 (d, ΔJ=21 Hz, 2H), 3.80 (s, 2H), 5.20–5.29 (p, 1H), 6.58 (s, 1H), 7.13–7.65 (m, 8H).

EXAMPLE 5

(3-endo)-9-Benzyl-9-azabicyclo[3.3.1]nonanyl-3-N-(2', 5'-dimethoxyphenyl)-carbamate (5)

A mixture of (3-endo)-9-benzyl-9-azabicyclo[3.3.1] nonanol (100 mg, 0.43 mmol) and the 2,5-dimethoxyphenyl isocyanate (78 mg, 0.43 mmol) in dry toluene (10 mL) was heated under reflux for 2 hours. After cooling, the organic solution was made alkaline with saturated sodium bicarbonate solution and then extracted with chloroform (3×20 mL). The organic layers were combined and dried with sodium sulfate. The solvent was removed under vacuum and the residue crystallized from pentane/ethylacetate to give the title compound.

NMR (CDCl$_3$)δ1.41–2.18 (m, 8H), 2.42–2.52 (m, 2H), 2.99–3.04 (d, ΔJ=15 Hz, 2H), 3.83 (s, 3H), 3.80 (s, 2H), 3.75 (s, 3H), 5.21–5.30 (p, 1H), 6.49–7.36 (m, 8H),7.85 (br s, 1H).

EXAMPLE 6

(3-endo)-9-Benzyl-9-azabicyclo[3.3.1]nonanyl -3-N-(5'-chloro-2', 4'-dimethoxyphenyl)carbamate (6)

A mixture of (3-endo)-9-benzyl-azabicyclo[3.3.1]nonanol (100 mg, 0.43 mmol) and the 5-chloro-2,4-dimethoxyphenyl isocyanate (91.85 mg, 0.43 mmol) in dry dichloromethane (10 mL) was stirred with dibutyltin diacetate (2 drops) for 12 hours. The organic solution was concentrated to dryness under vacuum. The resulting glassy oil was chromatographed on silica gel with EtOAc:hexane:triethylamine 1:1:0.02. The solvent was removed under vacuum and the residue crystallized from pentane/EtOAc to give the title compound.

NMR (CDCl$_3$) 67 1.45–2.22 (m, 8H), 2.50–2.55 (m, 2H), 3.01–3.06 (d, DJ=15 Hz, 2H), 3.84 (s, 3H), 3.82 (s, 2H), 3.75 (s, 3H), 5.24–5.30 (p, 1H), 6.97–7.36 (m, 7H), 8.04 (br s, 1H).

EXAMPLE 7

(3-endo)-9-Benzyl-9-azabicyclo[3.3.1]nonanyl-3-N-(5'-chloro-2'-methoxyphenyl)carbamate (7)

A mixture of (3 -endo)-9-benzyl-9-azabicyclo[3.3.1] nonanol (100 mg, 0.43 mmol) and the 5-chloro-2-methoxyphenyl isocyanate (78.94 mg, 0.43 mmol) in dry dichloromethane (10 mL) was stirred with dibutyltin diacetate (2 drops) for 12 hours. The organic solution was concentrated to dryness under vacuum. The resulting glassy oil was chromatographed on silica gel with EtOAc:hexane:triethylamine 1:1:0.02. The solvent was removed under vacuum and the residue crystallized from pentane/EtOAc to give the title compound.

NMR (CDCl$_3$) δ1.39–2.18 (m, 8H), 2.42–2.53 (m, 2H), 2.99–3.03 (d, DJ=15 Hz, 2H), 3.83 (s, 3H), 3.81 (s, 2H), 5.24–5.32 (p, 1H), 6.75–7.21 (m, 8H), 8.14 (br s, 1H).

EXAMPLE 8

(3-endo)-9-Methyl-9-azabicyclo[3.3.1]nonanyl-3-N-(3', 4'-dichlorophenyl)-carbamate (8)

A mixture of (3-endo)9-methyl-9-azabicyclo[3.3.1] nonanol (100 mg, 0.64 mmol) and the 3,4-dichlorophenyl isocyanate (121 mg, 0.64 mmol) in dry dichloromethane (10 mL) was stirred with dibutyltin diacetate (2 drops) for 12 hours. The organic solution was concentrated to dryness under vacuum. The resulting glassy oil was chromatographed on silica gel with EtOAc:hexane:triethylamine 1:1:0.02. The solvent was removed under vacuum and the residue crystallized from pentane/EtOAc to give the title compound.

NMR (CDCl$_3$) δ1.35–1.84 (m, 6H), 2.16–2.20 (m, 4H), 2.65 (s, 3H), 3.37–3.44 (m, 2H), 3.73 (s, 3H), 3.82 (s, 3H), 5.20–5.32 (p, 1H), 7.20–7.72 (m, 3H), 8.20 (br s, 1H).

EXAMPLE 9

(3-endo)-8-Benzyl-8azabicyclo[3.2.1]octyl-3-N-(2', 5'-dimethoxyphenyl)-carbamate (9)

A mixture of (3-endo)-8-benzyl-8-azabicyclo[3.2.1] octanol (100 mg, 0.46 mmol) and the 2,5-dimethoxyphenyl isocyanate (82 mg, 0.46 mmol) in dry dichloromethane (10 mL) was stirred with dibutyltin diacetate (2 drops) for 12 hours. The organic solution was concentrated to dryness under vacuum. The resulting glassy oil was chromatographed on silica gel with EtOAc:hexane: triethylamine 1:1:0.02. The solvent was removed under vacuum and the residue crystallized from pentane/EtOAc to give the title compound.

NMR (CDCl$_3$) d 1.80–3.22 (m, 8H), 3.64 (br s, 2H), 3.72 (s, 3H), 3.82 (s, 3H), 4.05 (s, 2H), 5.22–5.32 (m, 1H), 6.64–7.40 (m, 8H), 8.14 (br s, 1H).

EXAMPLE 10

(3-endo)-8-Benzyl-8-azabicyclo[3.2.1]octyl-3-N(3', 4'-dichlorophenyl)-carbamate (10)

A mixture of (3-endo)-8-benzyl-8-azabicyclo[3.2.1] octanol (100 mg, 0.46 mmol) and the 3,4-dichlorophenyl isocyanate (86 mg, 0.46 mmol) in dry dichloromethane (10 mL) was stirred with dibutyltin diacetate (2 drops) for 12 hours. The organic solution was concentrated to dryness under vacuum. The resulting glassy oil was chromatographed on silica gel with EtOAc:hexane:triethylamine 1:1:0.02. The solvent was removed under vacuum and the residue crystallized from pentane/EtOAc to give the title compound.

NMR (CDCl₃)δ1.79–3.20 (m, 8H), 3.66 (br s, 2H), 3.72 (s, 3H), 3.83 (s, 3H), 4.05 (s, 2H), 5.19–5.30 (m, 1H), 7.22–7.81 (m, 8H), 8.24 (br s, 1H).

EXAMPLE 11

(3-endo)-9-Methyl-9-azbicyclo[3.3.1]nonayl-3-N-(2', 5'-diethylphenyl)-carbamate (11)

A mixture of (3-endo)-9-methyl-9-azabicyclo[3.3.1] nonanol (100 mg, 0.64 mmol) and the 2,5-diethoxyphenyl isocyanate (114 mg, 0.64 mmol) in dry dichloromethane (10 mL) was stirred with dibutyltin diacetate (2 drops) for 12 hours. The organic solution was concentrated to dryness under vacuum. The resulting glassy oil was chromatographed on silica gel with EtOAc:hexane:triethylamine 1:1:0.02. The solvent was removed under vacuum and the residue crystallized from pentanc/EtOAc to give the title compound.

NMR (CDCl₃) δ1.40–1.87 (m, 6H), 2.15–2.20 (m, 4H), 2.61 (s, 3H), 3.37–3.41 (m, 2H), 3.82 (s, 3H), 3.73 (s, 3H), 5.24–5.33 (p, 1H), 6.75–7.21 (m, 3H), 8.10 (brs, 1H).

EXAMPLE 12

The ability of the above compounds to bind selectively to $\sigma_2$ receptors can be demonstrated by measuring their affinities to sigma receptors using known receptor binding assays (Mach et al., *Life Sciences*, 57 PL57–62 (1995)).

EXAMPLE 13
Pharmacological Studies
A. Sigma Receptor Binding

Sigma-1 binding sites were labeled with the $\sigma_1$-selective radioligand, [³H](+)-pentazocine (Dupont-NEN) in guinea pig brain membranes (Rockland Biological). Sigma-2 sites were assayed in rat liver membranes with [³H]DTG (Dupont-NEN) in the presence of (+)-pentazocine (100 nM). Sigma-2 site were also assayed in guinea pig membranes with [³H]DTG in the presence of (+)-pentazocine (100 nM).
B. σ1 Binding Assay Guinea pig brain membranes (100 μg protein) were incubated with 3 nM [³H](+)-pentazocine (31.6 Ci/mmol) in 50 mm Tris-HCl, pH 8.0 at 25° C. for either 120 or 240 minutes. Test compounds were dissolved in ethanol (7 concentrations ranging from 1–1000 nM) then diluted in buffer for a total incubation volume of 0.5 mL. Assays were terminated by the addition of ice-cold 10 mM Tris HCl, pH 8.0 followed by rapid filtration through Whatman GF/B glass fiber filters (presoaked in 0.5% polyethylenimine) using a Brandel cell harvester (Gaithersburg, Md.). Filters were washed twice with 5 ML of ice cold buffer. Nonspecific binding was determined in the presence of 10 μM (+)-pentazocine. Liquid scintillation counting was carried out in EcoLite (+) (ICN Radiochemicals; Costa Mesa, Calif.) using a Beckman LS 6000IC spectrometer with a counting efficiency of 50%. Typical counts were 70 dpm/μg protein for total binding, 6 dpm/μg protein for nonspecific binding, and 64 dpm/μg protein for specific binding.
C. σ2 Binding Assay Rat liver membranes (35 μg of protein) or guinea pig brain membranes (360 μg) were incubated with 3 nM [³H]DTG (38.3 Ci/mmol) in the presence of 100 nM (+)-pentazocine to mask σ1 sites. Incubations were carried out using the compound of Exs. 2–5 and the competitive antagonist (7 different concentrations ranging from 1–1000 nM) in 50 mM Tris-HCl, pH 8.0 for 120 minutes at 25° C. in a total incubation volume of 0.5 mL. Assays were terminated by the addition of ice-cold 10 mM Tris-HCl, pH 8.0 followed by rapid filtration through Whatman GF/B glass fiber filters (presoaked in 0.5% polyethylenimine) using a Brandel cell harvester (Gaithersburg, Md.). Filters were then washed twice with 5 mL of ice cold buffer Nonspecific binding was determined in the presence of 5 μM DTG. Liquid scintillation counting was carried out in EcoLite(+) (ICN Radiochemicals; Costa Mesa, Calif.) using a Beckman LS 6000IC spectrometer with a counting efficiency of 50%. Typical counts for rat liver were 297 dpm/μg protein for total binding, 11 dpm/μg protein for nonspecific binding, and 286 dpm/μg protein for specific binding. Typical counts for guinea pig brain were 16 dpm/μg protein for total binding, 2 dpm/μg protein for nonspecific binding, and 14 dpm/μg protein for specific binding.
D. Data Analysis The IC₅₀ values at sigma sites were determined in triplicate from non-linear regression of binding data as analyzed by JMP (SAS Institute; Cary, N.C.), using 5–10 concentrations of each compound. $K_i$ values were calculated using the Cheng-Prusoff equation and represent mean values ±SEM. All assays were done in triplicate unless otherwise noted. The $K_d$ value used for [³H]DTG in rat liver was 17.9 nM and was 4.8 nM for [³H](+)-pentazocine in guinea pig brain. The $K_d$ value for [³H]DTG in guinea pig brain was determined by separate Scatchard analyses to be 21.6 nM.
E. Results The in vitro binding data for compounds described in this patent application are shown in Table 2.

TABLE 2

| | $K_i$[nM] | |
|---|---|---|
| | $\sigma_1$ | $\sigma_2$ |
| Compound 2 | >1000 | 36.9 |
| Compound 3 | >1000 | 156.4 |
| Compound 4 | 33.3 | 91.9 |
| Compound 5 | 329.1 | 28.2 |
| Compound 6 | 189 | 22.9 |
| Compound 7 | >1000 | 63.5 |
| Compound 8 | 595 | 50.3 |
| Compound 9 | 72.4 | 22.1 |
| Compound 10 | 716 | 16.2 |

Generally compounds of the invention demonstrate high selectivity for $\sigma_2$ versus $\sigma_1$ receptors.

It is believed that compounds of formula I can provide detectably labeled ligands that can selectively bind to carrier cells and can be quantified by using functional imaging techniques such as positron emission tomography (PET), single photon emission computed tomography (SPECT), and functional magnetic resonance imaging (fMRI). Said components have the potential to noninvasively assess the proliferative status of known or suspected tumor cells or cells subject to hyperplasia, in bladder, colon, prostate, breast, lung, gut, pancreas, reproductive system, brain and the like. The labeled compounds of formula (I) can also be used to treat cancer or abnormally dividing cells, by selectively inhibiting their proliferation.

What is claimed is:

1. A method for determining the proliferative status of a tumor that comprises cells that express sigma-2 receptors, comprising:

(a) contacting the cells with a detectably labeled sigma-2 ligand, and (b) determining the extent to which the ligand binds to the cells, wherein the extent provides a measure of the proliferative status of the tumor.

2. The method of claim 1 wherein the detectably labeled sigma-2 ligand is suitable for imaging.

3. The method of claim 2 wherein the imaging comprises employing positron emission tomography or single photon emission computed tomography.

4. The method of claim 1 wherein the extent to which the ligand binds to the cells is determined by comparing the uptake in tumor tissue to the uptake in normal tissue.

5. The method of claim 1 wherein the tumor is located in the bladder, colon, prostate, breast, lung, gut pancreas, reproductive system, or brain.

6. A method to treat a human afflicted with a tumor or cancel comprising administering to the human, an effective amount of a compound of formula (I):

(I)

wherein

R is $(C_1-C_4)$alkyl, $C_6F_5CH_2$, and $T-C_6H_4CH_2$ wherein T is halo, $CH_3S$, $CH_3O$, $NH_2$ or H;

A is NH, O or S;

B is HN, O or S;

C is O or S;

D is CH;

E is CH;

F is CH;

Y and Z are individually H, halo, OH, $(C_1-C_4)$alkyl, $(C_1-C_4)$alkoxy, $(C_1-C_4)$alkylC(O), $(C_1-C_4)$alkyls, $NH_2$, SH, $N(R)_2$ or together are $OCH_2O$;

X is $(CH_2)_2$, $(CH_2)_3$ or CH=CH;

wherein alkyl can be straight chained, branched, cycloalkyl or (cycloalkyl)alkyl; or a phanmaceutically acceptable salt thereof.

7. A method to image a tumor comprising:

(a) administering to a human afflicted with a tumor, an amount of a detectably-labeled compound of formula (I):

(I)

wherein

R is $(C_1-C_4)$alkyl, $C_6F_5CH_2$, and $T-C_6H_4CH_2$ wherein T is halo, $CH_3S$, $CH_3O$, $NH_2$ or H;

A is NH, O or S;

B is HN, O or S;

C is O or S;

D is CH;

E is CH;

F is CH;

Y and Z are individually H, halo, OH, $(C_1-C_4)$alkyl, $(C_1-C_4)$alkoxy, $(C_1-C_4)$alkylC(O), $(C_1-C_4)$alkyls, $NH_2$, SH, $N(R)_2$ or together are $OCH_2O$;

X is $(CH_2)_2$, $(CH_2)_3$ or CH=CH;

wherein alkyl can be straight chained, branched, cycloalkyl or (cycloalkyl)alkyl;

which is detectably-labeled;

or a pharmaceutically acceptable salt thereof; effective to image the tumor; and (B) detecting the compound of formula (I) to identify the presence of the tumor.

8. The method of claim 7 wherein the detecting comprises employing positron emission tomography or single photon emission computed tomography.

9. A compound of formula (I):

(I)

wherein

R is $(C_1-C_4)$alkyl, $C_6F_5CH_2$, and $T-C_6H_4CH_2$ wherein T is halo, $CH_3S$, $CH_3O$, $NH_2$ or H;

A is NH, O or S;

B is HN, O or S;

C is O or S;

D is CH;

E is CH;

F is CH;

Y and Z are individually H, halo, OH, $(C_1-C_4)$alkyl, $(C_1-C_4)$alkoxy, $(C_1-C_4)$alkylC(O), $(C_1-C_4)$alkyls, $NH_2$, SH, $N(R)_2$ or together are $OCH_2O$;

X is $(CH_2)_2$, $(CH_2)_3$ or CH=CH;

wherein alkyl can be straight chained, branched, cycloalkyl or (cycloalkyl)alkyl;

which is detectably-labeled by appending a radioisotope of a halogen to the aromatic ring comprising DEF;
or a pharmaceutically acceptable salt thereof.

10. A compound of formula (I):

wherein

R is $(C_1-C_4)$alkyl, $C_6F_5CH_2$, and T—$C_6H_4CH_2$ wherein T is halo, $CH_3S$, $CH_3O$, $NH_2$ or H;

A is NH, O or S;

B is HN, O, or S;

C is O or S;

D is CH;

E is CH;

F is CH;

Y and Z are individually H, halo, OH, $(C_1-C_4)$alkyl, $(C_1-C_4)$alkoxy, $(C_1-C_4)$alkylC(O), $(C_1-C_4)$alkyls, $NH_2$, SH, $N(R)_2$ or together are $OCH_2O$;

X is $(CH_2)_2$, $(CH_2)_3$ or CH=CH;

wherein alkyl can be straight chained, branched, cycloalkyl or (cycloalkyl)alkyl;

which is detectably-labeled with a metal chelating, group comprising a radionuclide;

or a pharmaceutically acceptable salt thereof.

11. The compound of claim 10 wherein the metal chelating group is attached directly to a compound of formula (I), or the metal chelating group is attached to a compound of formula (I) by means of a divalent or bifunctional organic linker group.

12. The compound of claim 11 wherein the bifunctional linker group is 2-aminoethyl, 2-mercaptoethyl, 2-aminopropyl, 2-mercaptopropyl, ϵ-amino caproic acid, or 1,4-diaminobutane.

13. The compound of claim 10 wherein the radionuclide is a metallic radioisotope.

14. The compound of claim 11 wherein the bifunctional linker group is less than 50 angstroms in length.

15. A pharmaceutical composition comprising a compound of any one of claims 9–14 and a pharmaceutical acceptable carrier.

* * * * *

UNITED STATES PATENT AND TRADEMARK OFFICE
CERTIFICATE OF CORRECTION

PATENT NO. : 6,676,925 B1
DATED : January 13, 2004
INVENTOR(S) : Mach et al.

It is certified that error appears in the above-identified patent and that said Letters Patent is hereby corrected as shown below:

Title page,
Item [57], ABSTRACT, replace with the following:
-- Detectably-labeled compounds of formula (I) wherein A, B, C, D, E, F, R, X, Y and Z have any of the meanings given in the specification and their pharmaceutically acceptable salts, are useful in competitive assays to assay for the presence of α2 receptors. Also disclosed are pharmaceutical compositions containing such a compound of formula (I), methods for their use and intermediates useful for preparing such compounds of formula (I).

--

Column 1,
Lines 40-50, should read
--

--

UNITED STATES PATENT AND TRADEMARK OFFICE
CERTIFICATE OF CORRECTION

PATENT NO. : 6,676,925 B1
DATED : January 13, 2004
INVENTOR(S) : Mach et al.

Page 2 of 2

It is certified that error appears in the above-identified patent and that said Letters Patent is hereby corrected as shown below:

Column 2,
Line 52, should read --

--

Column 3,
Line 3, should read --

--

Column 7,
Line 64, should read -- NMR (CDCl$_3$) δ1.45-2.22 (m,8H), 2.50-2.55 (m,2H), --

Column 11,
Line 61, should read -- cycloalkyl or (cycloalkyl)alkyl; or a pharmaceutically --

Column 12,
Line 27, should read -- X is (CH$_2$)$_2$, (CH$_2$)$_3$ or CH=CH; --

Signed and Sealed this

Twentieth Day of July, 2004

JON W. DUDAS
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 6,676,925 B1 | Page 1 of 1 |
| APPLICATION NO. | : 09/528398 | |
| DATED | : January 13, 2004 | |
| INVENTOR(S) | : Mach et al. | |

It is certified that error appears in the above-identified patent and that said Letters Patent is hereby corrected as shown below:

In the Specification

Column 1, Line 10: Please insert the following:
--STATEMENT OF GOVERNMENT SUPPORT
This invention was made with government support under grant numbers CA045156 and NS031907 awarded by the National Institutes of Health. The government has certain rights in the invention.--

Signed and Sealed this
Twenty-third Day of September, 2025

John A. Squires
*Director of the United States Patent and Trademark Office*